United States Patent [19]

Mishina et al.

[11] Patent Number: 5,420,164
[45] Date of Patent: May 30, 1995

[54] CYCLOALKYLUREA COMPOUNDS

[75] Inventors: Tadashi Mishina; Kanou Harada; Joji Yasuoka; Hidenobu Kushuhara, all of Iruma; Noriyoshi Izumi, Chikujo, all of Japan

[73] Assignee: Yoshitomi Pharmaceutical Industries, Ltd., Japan

[21] Appl. No.: 55,251

[22] Filed: May 3, 1993

Related U.S. Application Data

[63] Continuation-in-part of Ser. No. 863,597, Apr. 3, 1992, abandoned.

[30] Foreign Application Priority Data

| Apr. 4, 1991 | [JP] | Japan | 3-100450 |
| Jul. 8, 1991 | [JP] | Japan | 3-194869 |
| Dec. 4, 1991 | [JP] | Japan | 3-348898 |

[51] Int. Cl.$^6$ .......... A61K 31/17; C07C 275/06; C07C 275/28; C07C 275/26
[52] U.S. Cl. .......... 514/596; 514/227.2; 514/239.5; 514/255; 514/275; 514/315; 514/353; 514/400; 514/426; 514/447; 514/461; 544/164; 544/297; 544/382; 546/244; 546/306; 548/196; 548/335.5; 548/557; 549/49; 549/480; 564/48
[58] Field of Search .......... 564/48, 55; 514/596

[56] References Cited

U.S. PATENT DOCUMENTS

| 3,683,001 | 8/1972 | Knowles | 260/465 D |
| 4,216,228 | 8/1980 | Yamada et al. | 424/322 |
| 4,387,105 | 6/1983 | DeVries et al. | 564/49 |
| 4,716,175 | 12/1987 | Hoefle et al. | 514/357 |

FOREIGN PATENT DOCUMENTS

| 0293880 | 12/1988 | European Pat. Off. |
| 0297610 | 1/1989 | European Pat. Off. |
| 0335375 | 3/1989 | European Pat. Off. |
| 0344425 | 3/1989 | European Pat. Off. |
| 0325397 | 7/1989 | European Pat. Off. |
| 0384320 | 8/1990 | European Pat. Off. |
| 0399422 | 11/1990 | European Pat. Off. |
| 0405233 | 1/1991 | European Pat. Off. |
| 1028818 | 5/1966 | United Kingdom |
| 2149394 | 6/1985 | United Kingdom |
| 91/13871 | 9/1991 | WIPO |

*Primary Examiner*—Shailendra Kumar
*Attorney, Agent, or Firm*—Wenderoth, Lind & Ponack

[57] ABSTRACT

A cycloalkylurea compound of the formula (I):

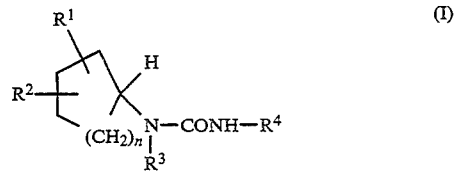

wherein each symbol is as defined in the specification, or a pharmaceutically acceptable salt thereof, which compound inhibits ACAT and is useful as hypolipidemic and antiatherosclerotic medicine.

8 Claims, No Drawings

CYCLOALKYLUREA COMPOUNDS

This is a continuation-in-part of Ser. No. 07/863,597, filed Apr. 3, 1992, now abandoned.

BACKGROUND OF THE INVENTION

The present invention relates to novel and pharmaceutically useful cycloalkylurea compounds or pharmaceutically acceptable salts thereof which inhibit acyl-CoA:cholesterol acyltransferase (ACAT) and are useful as hypolipidemic and anti-etherosclerotic medicines.

Hypercholesterolemia has been known to be a risk factor linked to lots of cardiovascular diseases. Increased level of plasma cholesterol may cause an accumulation of lipid-laden foam-cells at the artery wall, which is an early event in the development of atherosclerosis. Atherosclerosis would be the cause of many cardiovascular diseases including angina pectoris and myocardial infarction.

Cholesterol is esterified by microsomal acyl-CoA:-cholesterol acyltransferase (hereinafter referred to as ACAT) in intestinal mucosa. The esters are then incorporated into chylomicrons, which are secreted into the plasma through the lymph. ACAT inhibitors would inhibit the esterification of free cholesterol in diet and bile. Consequently, they are expected to decrease the plasma cholesterol level by the suppression of the entry of cholesterol into the body pool.

Atherosclerosis is pathologically distinctive for the appearance with the accumulation of lipids, especially cholesterol esters, at the artery wall. It has been demonstrated that the accumulation of cholesteryl esters is largely mediated by the formation of lipid-laden foam cells derived from macrophages. Since intracellular free cholesterol is also esterified by ACAT in macrophages, ACAT inhibitors would decrease the accumulation of cholesteryl esters in the cells. Therefore they are expected to prevent the formation of foam cells and the progression of atherosclerosis.

Compounds having ACAT inhibitory activity are disclosed in the literature, for example, 3-(2,4-difluorophenyl)-1-[(4-(2,2-dimethylpropyl)phenyl)methyl]-1-(heptyl)urea in GB 2149394, 2,2-dimethyl-N-(2,4,6-trimethoxyphenyl)dodecanamide in U.S. Pat. No. 4,716,175 and so on. A variety of N-phenyl-N'-cycloalkylurea derivatives having ACAT inhibitory activity can be found in, for example, U.S. Pat. No. 4,387,105; EP-A-293880; EP-A-297610; EP-A-325397; EP-A-384320; EP-A-394422; and WO91/13871. Diphenylurea derivatives having ACAT inhibitory activity are also known in EP-A-405233. Further N-phenyl-N'-cycloalkylurea compounds are known in U.S. Pat. 3683001, U.S. Pat. No. 4,216,228 and GB 1028818, but they are disclosed only as being useful animal repellants, fungicides and herbicides, respectively.

SUMMARY OF THE INVENTION

The object of the present invention is to provide therapeutically useful medicines for hypolipidemia and atherosclerosis. The present inventors have made intensive investigations with this view and found novel cycloalkylurea compounds having potent ACAT inhibitory activity and inhibitory activity on the formation of cholesteryl esters in cultured macrophages and some other cells. The novel compounds also lower serum and liver cholesterol in hyperlipidemic animals.

DETAILED DESCRIPTION OF THE INVENTION

The followings are provided by the present invention:

1. A cycloalkylurea compound of the formula (I):

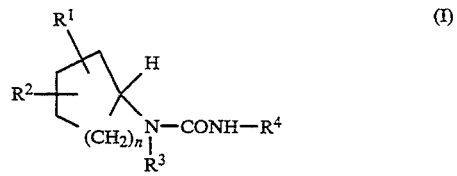

wherein $R_1$ is a group of the formula (a):

(wherein $R^6$, $R^7$ and $R^8$ are the same or different and each is hydrogen or alkyl having 1 to 8 carbon atoms, with the proviso that compounds wherein two or three of $R^6$, $R^7$ and $R^8$ are hydrogens are excluded), haloalkyl, cycloalkyl, alkoxy having 1 to 5 carbon atoms, phenyl, aralkyl or heteroaryl, or phenyl, aralkyl or heteroaryl each substituted on the aromatic ring by 1 to 3 substituents selected from alkyl having 1 to 4 carbon atoms, alkoxy having 1 to 8 carbon atoms, cycloalkyl, cycloalkyloxy, haloalkyl, haloalkoxy, halogen, nitro, amino and substituted amino;

$R^2$ is hydrogen, phenyl or phenyl substituted by 1 to 3 substituents selected from alkyl having 1 to 4 carbon atoms, alkoxy having 1 to 4 carbon atoms, haloalkyl and halogen, wherein $R^1$ and $R^2$ may be substituted on the same carbon atom of cycloalkyl ring;

$R^1$ and $R^2$ together may form a substituted or unsubstituted cyclic hydrocarbon having 3 to 7 carbon atoms or a substituted or unsubstituted spiran;

$R^3$ is hydrogen, alkyl having 1 to 8 carbon atoms, cycloalkyl, cycloalkylalkyl, alkoxyalkyl, alkylthioalkyl, aralkyl substituted by alkylenedioxy, aralkyl, aralkyloxyalkyl, aralkyl or aralkyloxyalkyl each substituted on the aromatic ring by 1 to 3 substituents selected from alkyl having 1 to 4 carbon atoms, alkoxy having 1 to 5 carbon atoms, halogen, nitro, hydroxy, amino, substituted amino, haloalkyl, alkylthio, benzyloxy and benzylthio, heteroarylalkyl, phenoxyalkyl, or heteroarylalkyl or phenoxyalkyl each substituted on the aromatic ring by 1 to 3 substituents selected from halogen, alkyl having 1 to 4 carbon atoms, alkoxy having 1 to 4 carbon atoms, nitro, amino and haloalkyl, or a group of the formula (c) or (d):

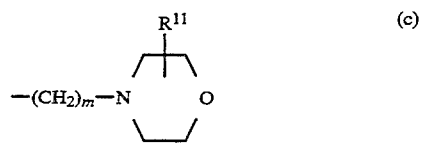

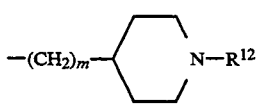

(d)

wherein m is 1 or 2, $R^{11}$ is hydrogen or alkyl having 1 to 4 carbon atoms, $R^2$ is hydrogen, alkyl having 1 to 4 carbon atoms or aralkyl;

$R^4$ is phenyl substituted by 1 to 3 substituents selected from alkyl having 1 to 4 carbon atoms, alkoxy having 1 to 4 carbon atoms, haloalkyl, halogen, amino and substituted amino;

n is 1, 2 or 3;

or a pharmaceutically acceptable salt thereof.

2. A compound as disclosed in the above-mentioned 1 wherein $R^1$ is phenyl or phenyl substituted by 1 to 3 substituents selected from alkyl having 1 to 4 carbon atoms, alkoxy having 1 to 8 carbon atoms, haloalkyl, halogen, nitro, amino and substituted amino; $R^2$ is phenyl or phenyl substituted by 1 to 3 substituents selected from alkyl having 1 to 4 carbon atoms, alkoxy having 1 to 4 carbon atoms, trifluoromethyl and halogen, wherein $R^1$ and $R^2$ may be substituted on the same carbon atom of cycloalkyl ring; or $R^1$ and $R^2$ together may form a substituted or unsubstituted cyclic hydrocarbon having 3 to 7 carbon atoms or a substituted or unsubstituted spiran; $R^3$ is hydrogen, alkyl having 1 to 8 carbon atoms, cycloalkyl, cycloalkylalkyl, aralkyl substituted by alkylenedioxy, aralkyl, aralkyl substituted on the aromatic ring by 1 to 3 substituents selected from alkyl having 1 to 4 carbon atoms, alkoxy having 1 to 5 carbon atoms, halogen, nitro, hydroxy, haloalkyl, alkylthio, benzyloxy and benzylthio, or heteroarylalkyl; $R^4$ is phenyl substituted by 1 to 3 substituents selected from alkyl having 1 to 4 carbon atoms, alkoxy having 1 to 4 carbon atoms, trifluoromethyl, halogen and substituted amino; n is 2; or a pharmaceutically acceptable salt thereof.

3. A compound as disclosed in the above-mentioned 1 wherein $R^1$ is secondary or tertiary alkyl having 3 to 5 carbon atoms, cycloalkyl or phenyl; $R^2$ is hydrogen; $R^3$ is hydrogen, alkyl having 1 to 8 carbon atoms, cycloalkyl, cycloalkylalkyl, aralkyl substituted by alkylenedioxy, aralkyl, aralkyl substituted on the aromatic ring by 1 to 3 substituents selected from alkyl having 1 to 4 carbon atoms, alkoxy having 1 to 5 carbon atoms, halogen, nitro, hydroxy, haloalkyl, alkylthio, benzyloxy and benzylthio, or heteroarylalkyl; $R^4$ is phenyl substituted by 1 to 3 substituents selected from alkyl having 1 to 4 carbon atoms, alkoxy having 1 to 4 carbon atoms and halogen; n is 2; or a pharmaceutically acceptable salt thereof.

4. In detail, a compound as disclosed in the above-mentioned 1 selected from the group consisting of
N-(2,6-diisopropylphenyl)-N'-(2-phenylcyclohexyl)urea,
N-(2,6-diisopropylphenyl)-N'-heptyl-N'-(4-phenylcyclohexyl)urea,
trans-N-(2,6-diisopropylphenyl)-N'-benzyl-N'-(4-phenylcyclohexyl)urea,
N-(2,6-diethylphenyl)-N'-benzyl-N'-(4-phenylcyclohexyl)urea,
N-(2,4-difluorophenyl)-N'-benzyl-N'-(4-phenylcyclohexyl)urea,
N-(2,6-diisopropylphenyl)-N'-(3,4-dimethoxybenzyl)-N'-(4-phenylcyclohexyl)urea,
N-(2,4,6-trimethoxyphenyl)-N'-benzyl-N'-(4-phenylcyclohexyl)urea,
N-(2,6-diisopropylphenyl)-N'-benzyl-N'-(4-tert-butylcyclohexyl)urea,
trans-N-(2,6-diisopropylphenyl)-N'-(2-methylbenzyl)-N'-(4-phenylcyclohexyl)urea,
trans-N-(2,6-diisopropylphenyl)-N'-(2-chlorobenzyl)-N'-(4-phenylcyclohexyl)urea,
N-(2,6-diisopropylphenyl)-N'-(2-phenylethyl)-N'-(4-phenylcyclohexyl)urea,
trans-N-(2,6-diisopropylphenyl)-N'-(3-phenylpropyl)-N'-(4-phenylcyclohexyl)urea,
trans-N-(2,6-diisopropylphenyl)-N'-(1,1'-bicyclohexyl-4-yl)urea,
trans-N-(2,6-diethylphenyl)-N'-cyclohexylmethyl-N'-(4-phenylcyclohexyl)urea,
trans-N-(2,6-diisopropylphenyl)-N'-cyclohexylmethyl-N'-(4-phenylcyclohexyl)urea,
N-(2,6-diisopropylphenyl)-N'-thenyl-N'-(4-phenylcyclohexyl)urea,
trans-N-(2,6-diisopropylphenyl)-N'-furfuryl-N'-(4-phenylcyclohexyl)urea,
N-(2,6-diethylphenyl)-N'-(2-methylbenzyl)-N'-(4-phenylcyclohexyl)urea,
N-(2,6-diethylphenyl)-N'-(2-chlorobenzyl)-N'-(4-phenylcyclohexyl)urea and
trans-N-(2,6-diisopropylphenyl)-N'-(2-pyridylmethyl)-N'-(4-phenylcyclohexyl)urea or a pharmaceutically acceptable salt thereof.

5. Preferably, a compound as disclosed in the above-mentioned 1 selected from the group consisting of
trans-N-(2,6-diisopropylphenyl)-N'-benzyl-N'-(4-phenylcyclohexyl)urea,
trans-N-(2,6-diisopropylphenyl)-N'-(2-methylbenzyl)-N'-(4-phenylcyclohexyl)urea,
trans-N-(2,6-diisopropylphenyl)-N'-(2-chlorobenzyl)-N'-(4-phenyl-cyclohexyl)urea and
trans-N-(2,6-diethylphenyl)-N'-cyclohexylmethyl-N'-(4-phenylcyclohexyl)urea,
or a pharmaceutically acceptable salt thereof.

6. Also preferably, a compound as disclosed in the above-mentioned 1 which is N-(2,6-diisopropylphenyl)-N'-(4,4-diphenylcyclohexyl)urea, or a pharmaceutically acceptable salt thereof.

7. A pharmaceutical composition consisting of an effective amount of the compound as disclosed in the above-mentioned 1 or a pharmaceutically acceptable salt thereof and pharmaceutical carriers.

The definitions of each symbols in the formula (I) are exemplified as follows:

In $R^1$, alkyl having 1 to 8 carbon atoms means, for example, methyl, ethyl, propyl, isopropyl, butyl, isobutyl, sec-butyl, tert-butyl, pentyl, hexyl, heptyl, octyl, 1-ethylpropyl or 2,2-dimethylpropyl; the group of formula (a) in $R^1$ means preferably secondary or tertiary alkyl having 3 to 12 carbon atoms and is exemplified by, for example, isopropyl, 1-methylpropyl, 1-methylbutyl, 1-ethylpropyl, tert-butyl, tert-pentyl, 1-methylhexyl, 1-methylheptyl, 1-methyloctyl, 1-methylnonyl, 1-ethylnonyl, 1,1-dimethylhexyl or 1,1-dimethylnonyl; haloalkyl has 1 to 8 carbon atoms in the alkyl moiety and is exemplified by, for example, fluoromethyl, trifluoromethyl, chloroethyl, 2,2,2-trifluoroethyl, perfluoroethyl, chloropropyl, chlorobutyl, chloropentyl, chlorohexyl or chloroheptyl; cycloalkyl has 3 to 7 carbon atoms and is exemplified by, for example, cyclopropyl, cyclobutyl, cyclopentyl, cyclohexyl or cycloheptyl, preferably cyclohexyl; alkyl having 1 to 4 carbon atoms means, for example, methyl, ethyl, propyl, isopropyl, butyl, isobutyl, sec-butyl or tert-butyl; alkoxy having 1 to 4 carbon atoms means, for example, methoxy, ethoxy, propoxy, isopropoxy, butoxy, isobutoxy, sec-butoxy or tert-butoxy; alkoxy having 5 carbon atoms means pentyloxy, isopentyloxy or tert-pentyloxy; alkoxy having 1 to 8 carbon atoms means hexyloxy, heptyloxy or octyloxy in addition to the alkoxy having 1 to 5 carbon atoms; haloalkoxy has 1 to 4 carbon atoms and is exemplified by, for example, fluoromethoxy, trifluoromethoxy, chloroethoxy, 2,2,2-trifluoroethoxy, perfluoroethoxy, chloropropoxy or chlorobutoxy; cycloalkyloxy has 3 to 7 carbon atoms in the cycloalkyl moiety and is exemplified by, for example, cyclopropyloxy, cyclobutyloxy, cyclopentyloxy, cyclohexyloxy or cycloheptyloxy; halogen means fluorine, chlorine, bromine or iodine; substituted amino means mono- or dialkylamino (e.g. methylamino, dimethylamino, ethylamino, diethylamino, propylamino, dipropylamino), acylamino (e.g. formylamino, acetylamino, propionylamino, butyrylamino, isobutyrylamino, benzoylamino), alkoxycarbonylamino (e.g. methoxycarbonylamino, ethoxycarbonylamino, propoxycarbonylamino), aralkyloxycarbonylamino (e.g. benzyloxycarbenylamino, 2-phenylethyloxycarbonylamino) or cyclic amino (e.g. pyrrolidinyl, piperidino, morpholino, thiomorpholino, 1-piperazinyl, 4-methyl-1-piperazinyl); aralkyl means, for example, benzyl, 1-phenylethyl, 2-phenylethyl, 1-phenylpropyl, 2-phenylpropyl, 3-phenylpropyl, 2-methyl-2-phenylpropyl, 4-phenylbutyl, 5-phenylpentyl, 1-naphthylmethyl or 1-(1-naphthyl)ethyl; heteroaryl means, for example, thienyl, pyridyl, furyl, pyrrolyl, oxazolyl, thiazolyl, imidazolyl, pyrazolyl, pyrimidinyl or indolyl.

Preferred groups of $R^1$ are secondary or tertiary alkyl having 3 to 5 carbon atoms (e.g isopropyl, 1-methylpropyl, 1-methylbutyl, 1-ethylpropyl, tert-butyl, tert-pentyl), cycloalkyl (e.g. cyclohexyl) and phenyl.

In $R^2$, alkyl having 1 to 4 carbon atoms, alkoxy having 1 to 4 carbon atoms, haloalkyl and halogen which are substituents of phenyl are exemplified by those mentioned in $R^1$. Preferred groups of $R^2$ are hydrogen, phenyl and phenyl substituted by halogen.

Substituted or unsubstituted cyclic hydrocarbon having 3 to 7 carbon atoms formed by $R^1$ and $R^2$ means, for example, cyclopropyl, cyclobutyl, cyclopentyl, cyclohexyl, cycloheptyl, methylcyclopentyl, methylcyclohexyl, ethylcyclohexyl or butylcyclohexyl, preferably cyclohexyl; substituted or unsubstituted spiran formed by $R^1$ and $R^2$ with cycloalkyl ring means, for example, spiro[5.5]undec-3-yl, spiro[4.5]dec-8-yl, spiro[4.5]dec-2-yl, spiro[2.5]oct-6-yl or spiro[4.5]dec-6-yl; the substituent(s) for cyclic hydrocarbon and spiran is(are) selected from alkyl having 1 to 4 carbon atoms, alkoxy having 1 to 4 carbon atoms, halogen, nitro and amino.

In $R^3$, alkyl having 1 to 8 carbon atoms, cycloalkyl and aralkyl are exemplified by those mentioned in $R^1$; cycloalkylalkyl has 3 to 7 carbon atoms in the cycloalkyl moiety and 1 to 4 carbon atoms in the alkyl moiety and is exemplified by, for example, cyclopropylmethyl, cyclopentylmethyl, cyclohexylmethyl, cycloheptylmethyl, 2-cyclohexylethyl or 3-cyclohexylpropyl; alkoxyalkyl has 1 to 4 carbon atoms in the alkoxy moiety and 1 to 4 carbon atoms in the alkyl moiety and is exemplified by, for example, methoxymethyl, methoxyethyl, methoxypropyl, methoxybutyl, ethoxymethyl, ethoxyethyl or ethoxypropyl; alkylthioalkyl has 1 to 4 carbon atoms in the alkylthio moiety and 1 to 4 carbon atoms in the alkyl moiety and is exemplified by, for example, methylthiomethyl, methylthioethyl, methylthiopropyl, methylthiobutyl, ethylthiomethyl, ethylthioethyl or ethylthiopropyl; aralkyl substituted by alkylenedioxy means (1,3-benzodioxol-5-yl)methyl or (1,4-benzodioxan-6-yl)methyl; aralkyloxyalkyl has 1 to 4 carbon atoms in the alkyl moiety and is exemplified by, for example, benzyloxymethyl, 2-benzyloxyethyl, 3-benzyloxypropyl, 2-phenylethoxymethyl or 2-(2-phenylethoxy)ethyl; heteroarylalkyl has 1 to 4 carbon atoms in the alkyl moiety and is exemplified by, for example, thenyl, 2-, 3- or 4-pyridylmethyl, 2-(2-pyridyl)ethyl, furfuryl, 2-(2-furyl)ethyl or 2-pyrimidinylmethyl; phenoxyalkyl has 1 to 4 carbon atoms in the alkyl moiety and is exemplified by, for example, phenoxymethyl, 2-phenoxyethyl, 3-phenoxypropyl or 4-phenoxybutyl.

With regard to substituents in $R^3$, alkyl having 1 to 4 carbon atoms, alkoxy having 1 to 5 carbon atoms, halogen, substituted amino and haloalkyl are exemplified by those mentioned in $R^1$; alkylthio has 1 to 4 carbon atoms in the alkyl moiety and is exemplified by, for example, methylthio, ethylthio, propylthio, isopropylthio or butylthio; alkyl having 1 to 4 carbon atoms and aralkyl which are represented by $R^{11}$ or $R^{12}$ in the formulas (c) and (d) are exemplified by those mentioned in $R^1$.

Preferred groups of $R^3$ are hydrogen, alkyl having 1 to 8 carbon atoms, cycloalkyl, cycloalkylalkyl, aralkyl substituted by alkylenedioxy, aralkyl, aralkyl substituted on the aromatic ring by 1 to 3 substituents selected from alkyl having 1 to 4 carbon atoms, alkoxy having 1 to 5 carbon atoms, halogen, nitro, hydroxy, haloalkyl, alkylthio, benzyloxy and benzylthio, or heteroarylalkyl.

More preferred groups of $R^3$ are cycloalkyl (e.g. cyclohexyl), cycloalkylalkyl (e.g. cyclohexylmethyl), aralkyl (e.g. benzyl, 2-phenylethyl, 3-phenylpropyl, 4-phenylbutyl) and aralkyl substituted on the aromatic ring by substituent(s) (e.g. 2-chlorobenzyl, 2-fluorobenzyl, 2-methylbenzyl, 2-bromobenzyl, 2-methoxybenzyl, 2-ethoxybenzyl, 2-methylthiobenzyl, 2-(2-chlorophenyl)ethyl).

In $R^4$, alkyl having 1 to 4 carbon atoms, alkoxy having 1 to 4 carbon atoms, haloalkyl, halogen and substituted amino which are substituents of phenyl are exemplified by those mentioned in $R^1$.

Preferred groups of $R^4$ are phenyl substituted by 1 to 3 substituents selected from alkyl having 1 to 4 carbon atoms, alkoxy having 1 to 4 carbon atoms and halogen;

More preferred groups of $R^4$ are 2,6-diethylphenyl, 2,6-diisopropylphenyl, 2,4-difluorophenyl and 2,4,6-trimethoxyphenyl.

The pharmaceutically acceptable salts of the compounds of formula (I) include salts with an inorganic acid such as hydrochloric acid, hydrobromic acid, sulfuric acid etc., or with an organic acid such as acetic acid, fumaric acid, maleic acid, benzoic acid, citric acid, malic acid, methanesulfonic acid, benzenesulfonic acid etc. The present invention also includes hydrates and solvates of the compounds of formula (I).

In the compounds of formula (I), there exist compounds having cis- or trans-configuration between the urea group and the substituents: $R^1$ or $R^2$ regarding the cycloalkyl ring. The present invention embraces cis- and trans-isomers and the mixture thereof. When the compounds of the present invention have one or more asymmetric center, there exist a variety of optical isomers. The individual optical isomers, racemate thereof and diastereomer or the mixture thereof are encompassed in the present invention.

The compounds of the present invention can be prepared by, for example, the following methods outlined in Reaction Scheme.

Reaction Scheme

Method A

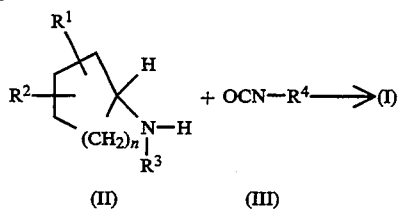

(II)     (III)

Method B

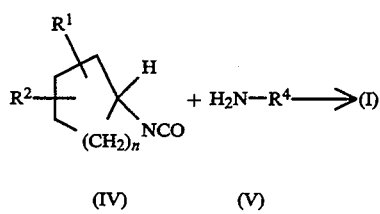

(IV)     (V)

Method C

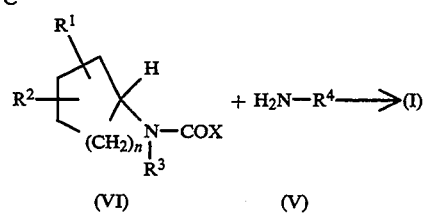

(VI)     (V)

(In the above formulas, X is halogen, and other symbols are as defined above.)

Method A

The compounds of formula (I) can be synthesized by reacting a cycloalkylamine of the formula (II) or a salt thereof with an isocyanic ester of the formula (III) in an appropriate solvent. Any solvent inert to the reaction can be used as the solvent. Thus, for example, use may be made of ethers such as diethyl ether, diisopropyl ether, dimethoxyethane or tetrahydrofuran; aromatic hydrocarbons such as benzene, toluene or xylene; esters such as methyl acetate or ethyl acetate; ketones such as acetone or methyl ethyl ketone; halogenated hydrocarbons such as dichloromethane, chloroform or dichloroethane; N,N-dimethylformamide; acetamide; acetonitrile; dimethyl sulfoxide and pyridine. The reaction may be carried out at any temperature between $-20°$ C. and $150°$ C., preferably between $0°$ C. and $100°$ C. The reaction will be significantly proceeded in the presence of a base such as triethylamine, N-methylmorpholine, diisopropylethylamine, 1,4-diazabicyclo[2.2.2]octane, pyridine, picoline, 4-dimethylaminopyridine, 4-(1-pyrrolidinyl)pyridine or N,N-dimethylaniline.

Method B

The compounds of formula (I) wherein $R^3$ is hydrogen can be synthesized by reacting an isocyanic ester of the formula (IV) with an amine of the formula (V) under similar conditions as in Method A.

Method C

The compounds of formula (I) wherein $R^3$ is the substituent other than hydrogen can be synthesized by reacting a carbamoyl halide of the formula (VI) with an amine of the formula (V) under similar conditions as in Method A.

The starting compounds, i.e. cycloalkylamine of the formula (II), can be synthesized by per se known methods.

The compounds of formula (I) can be converted into the above-mentioned pharmaceutically acceptable salts by treating them with an inorganic or an organic acid in a conventional manner.

Among the compounds of formula (I), there exist cis- and trans-isomers. They can be synthesized respectively by using cis- and trans-compounds of the formula (II), (IV) or (VI) as the starting compound. When the obtained compound is a mixture thereof, it can be separated into cis- and trans-isomers by means of a conventional method such as recrystallization or chromatography. The compounds of the present invention having a asymmetric center are usually obtained as racemates. The racemates can be resolved into the optical isomers by a conventional method such as fractional recrystallization or chromatography, or each optical isomer can be produced by employing the optically active starting compounds. The compounds having two or more asymmetric centers are usually obtained as each diastereomers or a mixture thereof. Each diastereomers can be resolved by means of fractional recrystallization or chromatography.

The following pharmacological experiments will illustrate that the compounds of the present invention have potent ACAT inhibitory activity and hypolipidemic activity.

Pharmacological Experiment 1: ACAT inhibitory activity

ACAT activity was determined according to the method of Heider et al. [J. Lipid Res., 24, 1127 (1983)]. Microsomes from intestinal mucosa of male Japanese White rabbits fed with 2% cholesterol-supplemented chow were used as the enzyme. The mixture of 0.154M potassium phosphate buffer (pH 7.4), containing [$^{14}$C]oleoyl-CoA, bovine serum albumin and test compounds were preincubated at $37°$ C. for 5 min before the addition of the enzyme. The mixture was incubated for 3 min. The reaction was stopped by the addition of she mixture of chloroform and methanol (2:1). After centrifugation, the chloroform phase was collected and dried. The residue was dissolved in n-hexane and spotted onto silica gel plates for thin layer chromatography (TLC). After the plates were developed, radioactivity in cholesteryl ester fraction was measured by using radio-TLC analyzer.

As a result, the compounds of the present invention have been found to have potent ACAT inhibitory activity with $IC_{50}$ values ranging from about 10 nM to about 50 nM.

Pharmacological Experiment 2: Cholesterol-lowering activity

Male Lewis rats were fed a diet supplemented with 1.5% cholesterol, 0.5% cholic acid and 10% coconut oil. Test compounds were added into a diet. After 3 days, total cholesterol in serum and liver was determined by enzymatic assay.

As a result, the test compounds caused significant decrease in serum and liver cholesterol levels in the cholesterol-loaded rats compared with those of control group. The same tests were conducted using mice and rabbits and the results similar to those in rats were observed.

As is clear from the foregoing pharmacological experiments, the compounds of the present invention exhibit potent ACAT inhibitory activity and cause significant decrease in serum and liver cholesterol levels in hyperlipidemic animals such as rats, mice or rabbits.

Pharmacological Experiment 3: Inhibition of cholesterol esterification in cultured macrophages Cholesterol esterification activity in macrophages, which has been known to be stimulated by modified LDL, was determined according to the method of Brown etal. (J. Biol. Chem., 255, 9344 (1980)). The peritoneal macrophages from male ddY mice were preincubated with test compounds at 37° C. for 2 hours under 5% $CO_2$/95% air. They were then incubated with [1-$^{14}$C]oleic acid, bovine serum albumine and acetylated LDL for 5 hours. The reaction was stopped and the intracellular lipids were extracted with hexane-propanol (3:2). Radioactivity in cholesteryl ester was measured as descrived in the Experiment 1. As a result, the compounds of the present invention have been found to be potent inhibitors of cholesterol esterification in macrophages. $IC_{50}$ values of the compounds were from $10^{-7}$ to $10^{-9}$M.

Pharmacological Experiment 4: Acute toxicity

The compounds of Examples 53 and 78 were orally administered to six male mice at the dosage of 1000 mg/kg, and no death occurrences were observed for 7 days.

The compounds of the present invention are potent ACAT inhivitors. They suppress the formation of cholesteryl esters in cultured macrophages and some other cells. They decrease serum and liver cholesterol levels in hyperlipidemic animals and are expected to suppress the absorption of cholesterol at intestinal mucosa and decrease the serum cholesterol level in human. They are also expected to suppress the cholesteryl ester formation in macrophages and prevent the accumulation of lipids in the artery wall. It has been shown that they have advantageous characters, concerning absorption through oral administration, bioavailability, duration time and safety. Therefore new hypolipidemic and anti-etherosclerotic medicines with high safety and potent activity would be obtained through the present invention.

The compounds of the present invention can be safely administered orally or parentorally to human beings in the form of pharmaceutical compositions such as powders, tablets, capsules, granules, suppositories or injectable solutions. The pharmaceutical composition can be prepared by mixing a therapeutically effective amount of the compound with a pharmaceutically acceptable additives such as carrier, excipient or diluent. The dose may vary depending upon the body weight, the severity of the patient to be treated or the age of the patient, but the daily dose for human adults preferably ranges 10 mg to 500 mg in single or multiple dose.

EXAMPLE

The present invention will be explained in more detail by the following examples, but these are not to be construed as limiting the present invention.

Example 1

To a solution of 1.6 g of 4-tert-butylcyclohexylamine in 15 ml of dichloromethane was added a solution of 2.2 g of 2,6-diisopropylphenylisocyanate in dichloromethane dropwise in the presence of pyridine at 0° C. Thereafter the mixture was stirred for 1.5 hours at room temperature and concentrated. The residue was partitioned between isopropyl ether and water, and the organic layer was successively washed with 0.5N hydrochloric acid, water and sodium sulfate solution. The organic layer was dried over magnesium sulfate and then distilled away. The resulting residue was crystallized from ethyl acetate to give 2.2 g of N-(2,6-diisopropylphenyl)-N'-(4-tert-butylcyclohexyl)urea, melting at 270° C.

Example 2

The reaction and procedure were conducted in the same manner as in Example 1 using 1.0 g of trans-4-tert-butylcyclohexylamine to give 0.5 g of trans-N-(2,6-diisopropylphenyl)-N'-(4-tert-butylcyclohexyl)urea, melting at 264°–266° C.

Example 3

The reaction and procedure were conducted in the same manner as in Example 1 using cis-4-tert-butylcyclohexylamine to give cis-N-(2,6-diisopropylphenyl)-N'-(4-tert-butylcyclohexyl)urea, melting at 179°–180.5° C.

Example 4

To a solution of 1 g of 4-phenylcyclohexylamine in 10 ml of dichloromethane was added 2,6-diethylphenylisocyanate dropwise in the presence of pyridine and the mixture was stirred for 2 hours at room temperature. To the resultant mixture was added 30 ml of diluted hydrochloric acid and the solution was extracted with chloroform. The extract was washed with water, aqueous sodium hydrogencarbonate solution and saturated brine, and then dried over magnesium sulfate. The solvent was distilled away and the residue was crystallized from methanol to give 0.4 g of N-(2,6-diethylphenyl)-N'-(4-phenylcyclohexyl)urea, melting at 247°–249° C.

Example 5

The reaction and procedure was conducted in the same manner as in Example 1 using 1.5 g of 2-phenylcyclohexylamine to give 1.2 g of N-(2,6-diisopropylphenyl)-N'-(2-phenylcyclohexyl)urea, melting at 225°–226° C.

Example 6

To a solution of 1.6 g of 4-isopropylcyclohexylisocyanate in chloroform is added a solution of 1.8 g of 2,4,6-trimethoxyaniline in chloroform dropwise in the presence of pyridine. The mixture is stirred at room temperature until starting compounds disappear on TLC. The resultant mixture is concentrated and the residue is dissolved in ethyl acetate. The solution is washed with diluted hydrochloric acid, aqueous sodium hydrogencarbonate solution and brine. The organic layer is dried over magnesium sulfate and filtered off. The filtrate is distilled away and the resulting residue is crystallized to give N-(2,4,6-trimethoxyphenyl)-N'-(4-isopropylcyclohexyl)urea.

Example 7

To a solution of 0.82 g of 2-tert-butyl-6-methylaniline in pyridine is added a solution of 1.2 g of N-methyl-N-(2-phenylcyclohexyl)carbamoylchloride in dichloromethane dropwise. The mixture is stirred at room temperature until starting compounds disappear on TLC.

The mixture is concentrated and the residue is dissolved in ethyl ether. The solution is washed with diluted hydrochloric acid, aqueous sodium hydrogencarbonate solution and brine. The organic layer is dried over sodium sulfate and filtered off. The filtrate is distilled away and the resuling residue is crystallized to give N-(2-tert-butyl-6-methylphenyl)-N'-methyl-N'-(2-phenylcyclohexyl)urea.

The following compounds can be prepared in a similar manner as the above examples.

(8) N-(2,4-difluorophenyl)-N'-(4,4-bis(4-chlorophenyl)cyclohexyl)urea, melting at 190°–191° C.

(9) N-(2,4-dimethoxyphenyl)-N'-(4,4-bis(4-chlorophenyl)cyclohexyl)urea, melting at 145°–147° C.

(10) N-(2,4-difluorophenyl)-N'-(4,4-diphenylcyclohexyl)urea, melting at 250°–252° C.

(11) N-(3-methylphenyl)-N'-(4,4-bis(4-chlorophenyl)-cyclohexyl)urea, melting at 150°–152° C.

(12) N-(3-trifluoromethylphenyl)-N'-(4,4-bis(4-chlorophenyl)cyclohexyl)urea, melting at 178°–180° C.

(13) N-(3-methoxyphenyl)-N'-(4,4-bis(4-chlorophenyl)cyclohexyl)urea, melting at 138°–140° C.

(14) N-(4-bromophenyl)-N'-(4,4-bis(4-chlorophenyl)-cyclohexyl)urea, melting at 199°–202° C.

(15) N-(2-ethylphenyl)-N'-(4,4-bis(4-chlorophenyl)-cyclohexyl)urea, melting at 150°–152° C.

(16) N-(2,4-dichlorophenyl)-N'-(4,4-diphenylcyclohexyl)urea, melting at 235°–237° C.

(17) N-(2,4-difluorophenyl)-N'-heptyl-N'-(4,4-bis(4-chlorophenyl)cyclohexyl)urea, melting at 86°–90° C.

(18) N-(3-trifluoromethylphenyl)-N'-(4,4-bis(4-chlorophenyl)cyclohexyl)-N'-heptylurea, melting at 138°–140° C.

(19) N-(3-trifluoromethylphenyl)-N'-(4,4-diphenylcyclohexyl)urea, melting at 236°–238° C.

(20) N-(2,6-diisopropylphenyl)-N'-(4,4-bis(4-chlorophenyl)cyclohexyl)urea, melting at 255°–257° C.

(21) N-(2,6-diisopropylphenyl)-N'-(decahydro-2-naphthyl)urea, melting at 229° C.

(22) N-(2,6-diisopropylphenyl)-N'-(4-phenylcyclohexyl)urea, melting at 195°–196° C.

(23) N-(2,6-diethylphenyl)-N'-(4,4-diphenylcyclohexyl)urea, melting at 206°–207° C.

(24) N-(2,6-diisopropylphenyl)-N'-(4,4-diphenylcyclohexyl)urea, melting at 243°–244° C.

(25) N-(2,6-diisopropylphenyl)-N'-(3-phenylcyclohexyl)urea, melting at 214°–215.5° C.

(26) N-(2,6-diethylphenyl)-N'-(2-phenylcyclohexyl)urea, melting at 249°–250° C.

(27) N-(2,6-diisopropylphenyl)-N'-(4-tert-butylcyclohexyl)-N'methylurea, melting at 256°–258° C.

(28) N-(2,4-difluorophenyl)-N'-(4-tert-butylcyclohexyl)urea, melting at 225°–227° C.

(29) N-(2,6-diisopropylphenyl)-N'-(spiro[5.5]undec-3-yl)urea, melting at 249.5° C.

(30) N-(2,6-diisopropylphenyl)-N'-(4-(4-pyridyl)cyclohexyl)urea ¼ hydrate, melting at 276°–277° C.

(31) N-(2,6-diisopropylphenyl)-N'-(4-tert-butylcyclohexyl)-N'-octylurea

(32) N-(2,6-diisopropylphenyl)-N'-(spiro[2.5]oct-6-yl)urea

(33) N-(2,6-diethylphenyl)-N'-(2-dicyclohexylyl)urea

(34) N-(2,6-diisopropylphenyl)-N'-(4-cyclopropylmethylcyclohexyl)urea

(35) N-(2,6-diethylphenyl)-N'-(4-(2-phenylethyl)cyclohexyl)urea

(36) N-(2-isopropyl-6-methylphenyl)-N'-(2-(2-thienyl)cyclopentyl)urea

(37) N-(2,6-diisopropylphenyl)-N'-(2-tert-butylcyclohexyl)urea

(38) N-(2,4,6-trimethoxyphenyl)-N'-(2-(4-isopropylphenyl)cyclohexyl)urea

(39) N-(2,4,6-trimethylphenyl)-N'-(4-(1-ethylpropyl)-cyclohexyl)urea

(40) N-(4-dimethylaminophenyl)-N'-(3-(4-butoxyphenyl)cyclopentyl)urea

(41) N-(4-acetylaminophenyl)-N'-(4-(4-nitrobenzyl)-cycloheptyl)-N'-benzylurea

(42) N-(2-tert-butyl-6-methylphenyl)-N'-(4-(1,1-dimethyloctyl)cyclohexyl)urea

(43) N-(2,6-diisopropylphenyl)-N'-(4-tert-butylcyclohexyl)-N'-heptylurea, melting at 169°–170° C.

(44) N-(2,6-diisopropylphenyl)-N'-(bicyclo[4.4.0]dec-2-yl)urea, melting at 217°–218° C.

(45) N-(2,6-diisopropylphenyl)-N'-(4-(4-hexyloxyphenyl)cyclohexyl)urea, melting at 225°–226° C.

(46) N-(2,6-diisopropylphenyl)-N'-heptyl-N'-(4-phenylcyclohexyl)urea, melting at 143°–144° C.

(47) N-(4-dimethylaminophenyl)-N'-(4-tert-butylcyclohexyl)urea, melting at 141°–142° C.

(48) cis-N-(2,6-diisopropylphenyl)-N'-(2-phenylcyclohexyl)urea, melting at 187°–189° C.

(49) N-(2,6-diisopropylphenyl)-N'-benzyl-N'-(4-phenylcyclohexyl)urea, melting at 144°–146° C.

(50) N-(2,6-di-tert-butylphenyl)-N'-(4-tert-butylcyclohexyl)urea

Example 51

A solution of 5 g of 4-phenylcyclohexanone and cyclohexylmethylamine in 100 ml of benzene was refluxed for 2 hours with removing water and the solvent was distilled away in vacuo. The residue was dissolved in methanol and to the solution was added 1.5 g of sodium borohydride. The mixture was stirred at room temperature and the solvent was distilled away in vacuo. To the residue was added water and extracted with diethyl ether. The organic layer was washed with saturated brine and dried over magnesium sulfate. The solvent was distilled away to give 7 g of N-(4-phenylcyclohexyl)-N-cyclohexylmethylamine as an oil. (N-(4-phenylcyclohexyl)-N-cyclohexylmethylamine hydrochloride, melting at 267°–270° C. with decomposition)

To the solution of 2 g of N-(4-phenylcyclohexyl)-N-cyclohexylmethylamine in dichloromethane was added 2 ml of pyridine and to the mixture was added a solution of 1.6 g of 2,6-diethylphenylisocyanate in 30 ml of dichloromethane dropwise. After the mixture was stirred at room temperature, to the solution was added diluted hydrochloric acid and extracted with ethyl acetate. The extract was washed with water, aqueous sodium hydrogencarbonate solution and saturated brine and then dried over magnesium sulfate. The solvent was distilled away in vacuo to give 2 g of crude crystals. The crystals were recrystallized from the mixture of ethyl acetate and hexane to give 1.2 g of N-(2,6-diethylphenyl)-N'-cyclohexylmethyl-N'-(4-phenylcyclohexyl)urea, melting at 166°–168° C.

Example 52

A solution of 5 g of 4-phenylcyclohexanone and benzylamine in 100 ml of benzene was refluxed with removing water and the mixture was concentrated in vacuo. The residue was dissolved in tetrahydrofuran and to the solution was added the equivalent weight of sodium bis(2-methoxyethoxy)aluminum hydride (70% toluene solution) under ice cooling. After completion of the reaction, to the mixture was added ammonium chloride solution and extracted with diethyl ether. The organic layer was washed with saturated brine and dried over magnesium sulfate. The solvent was distilled away to give 6.5 g of oil. The oil was chromatographed on a silica gel column using a mixture of hexane and ethyl acetate (20:1) as an eluent to give 3.9 g of cis-N-benzyl-N-(4-phenylcyclohexyl)amine. (cis-N-benzyl-N-(4-phenylcyclohexyl)amine hydrochloride, melting at 208°–210° C. with decomposition)

To a solution of 400 mg of cis-N-benzyl-N-(4-phenylcyclohexyl)amine in 20 ml of dichloromethane were added 2 ml of pyridine and then a solution of 310 mg of 2,6-diisopropylphenylisocyanate in 5 ml of dichloromethane dropwise. The mixture was stirred at room temperature, poured into diluted hydrochloric acid and extracted with ethyl acetate. The extract was washed with water, aqueous sodium hydrogencarbonate solution and saturated brine and then dried over magnesium sulfate. The solvent was distilled away in vacuo to give crude crystals. The crystals were recrystallized from the mixture of ethyl acetate and hexane to give 460 mg of cis-N-(2,6-diisopropylphenyl)-N'-benzyl-N'-(4-phenylcyclohexyl)urea, melting at 153°–154° C.

Example 53

A solution of 50 g of 4-phenylcyclohexanone and 30.7 g of benzylamine in 250 ml of benzene was refluxed for 3 hours with removing water and the solvent was distilled away in vacuo. The residue was dissolved in methanol and to the solution was added 10.8 g of sodium borohydride. The mixture was stirred at room temperature and the solvent was distilled away in vacuo. To the residue was added water and extracted with ethyl acetate. The organic layer was washed with water and saturated brine and dried over magnesium sulfate. The solvent was distilled away and ethyl acetate was added to the resulting oil. To the solution was added conc. hydrochloric acid and the precipitated crystals were collected by filtration. The crystals were recrystallized from the mixture of ethyl acetate and methanol to give 40.3 g of trans-N-benzyl-N-(4-phenylcyclohexyl)amine hydrochloride, melting at 244°–248° C. with decomposition.

75.4 g of trans-N-benzyl-N-(4-phenylcyclohexyl)amine hydrochloride was poured into aqueous sodium hydroxide solution and extracted with ethyl acetate. The extract was washed with water, dried and the solvent was distilled away. The residue was dissolved in 600 ml of dichloromethane and to the solution was added 60 ml of pyridine, and then added a solution of 51 g of 2,6-diisopropylphenylisocyanate in 100 ml of dichloromethane dropwise. After completion of the reaction, the solution was poured into diluted hydrochloric acid and extracted with ethyl acetate. The extract was washed with water, sodium hydrogencarbonate solution and saturated brine and then dried over magnesium sulfate. The solvent was distilled away in vacuo to give crude crystals. The crystals were recrystallized from the mixture of ethyl acetate and hexane to give 73 g of trans-N-(2,6-diisopropylphenyl)-N'-benzyl-N'-(4-phenylcyclohexyl)urea, melting at 148°–149° C.

(54) N-(2,6-diisopropylphenyl)-N'-(1,1'-bicyclohexyl-4-yl)urea, melting at 259°–261° C.

(55) N-(2,6-diethylphenyl)-N'-benzyl-N'-(4-phenylcyclohexyl)urea, melting at 148°–150° C.

(56) N-(2,4-difluorophenyl)-N'-benzyl-N'-(4-phenylcyclohexyl)urea, melting at 140°–142° C.

(57) N-(2,6-diisopropylphenyl)-N'-(1,1'-bicyclohexyl-2-yl)urea, melting at 226° C.

(58) N-(2,5-dimethoxyphenyl)-N'-(4-tert-butylcyclohexyl)urea, melting at 189°–191° C.

(59) cis-N-(2,6-diisopropylphenyl)-N'-(2-phenylcyclohexyl)urea, melting at 138°–140° C.

(60) trance-N-(2,6-diisopropylphenyl)-N'-(3,4-dimethoxybenzyl)-N'-(4-phenylcyclohexyl)urea, melting at 129°–130° C. (as crystals containing 1 molecule of ethanol)

(61) N-(2,4,6-trimethoxyphenyl)-N'-benzyl-N'-(4-phenylcyclohexyl)urea, melting at 188°–190° C.

(62) N-(2,4,6-trimethoxyphenyl)-N'-(2-phenylcyclohexyl)urea, melting at 182°–183° C.

(63) cis-N-(2,6-diisopropylphenyl)-N'-(1,1'-bicyclohexyl-4-yl)urea, melting at 208° C.

(64) N-(2,6-diisopropylphenyl)-N'-benzyl-N'-(4-tert-butylcyclohexyl)urea, melting at 155°–159° C.

(65) trans-N-(2,6-diisopropylphenyl)-N'-(2-methylbenzyl)-N'-(4-phenylcyclohexyl)urea, melting at 158°–160° C.

(66) trans-N-(2,6-diisopropylphenyl)-N'-(2-chlorobenzyl)-N'-(4-phenylcyclohexyl)urea, melting at 197°–198° C.

(67) N-(2,6-diisopropylphenyl)-N'-(4-nitrobenzyl)-N'-(4-phenylcyclohexyl)urea, melting at 214°–216° C.

(68) N-(2,6-diisopropylphenyl)-N'-(3-phenylpropyl)-N'-(4-phenylcyclohexyl)urea, melting at 196°–197.5° C.

(69) N-(2,6-diisopropylphenyl)-N'-(2-phenylethyl)-N'-(4-phenylcyclohexyl)urea, melting at 157°–159° C.

(70) cis-N-(2,6-diisopropylphenyl)-N'-benzyl-N'-(1,1'-bicyclohexyl-4'-yl)urea, melting at 139° C.

(71) N-(2,4,6-trimethoxyphenyl)-N'-(4-phenylcyclohexyl)urea, melting at 166.5°–168° C.

(72) N-(2,6-diisopropylphenyl)-N'-cyclohexyl-N'-(4-phenylcyclohexyl)urea, melting at 58°–62° C.

(73) cis-N-(2,6-diisopropylphenyl)-N'-(3-phenylpropyl)-N'-(4-phenylcyclohexyl)urea, melting at 147°–149° C.

(74) trans-N-(2,6-diisopropylphenyl)-N'-(5-phenylpropyl)-N'-(4-phenylcyclohexyl)urea, melting at 195°–196° C.

(75) trans-N-(2,6-diisopropylphenyl)-N'-(1,1'-bicyclohexyl-4-yl)urea, melting at 283.5°–284° C.

(76) trans-N-(2,6-diisopropylphenyl)-N'-benzyl-N'-(1,1'-bicyclohexyl-4-yl)urea, melting at 154°–155° C.

(77) trans-N-(2.6-diisopropylphenyl)-N'-(1,3-benzodioxol-5-yl)methyl-N'-(1,1'-bicyclohexyl-4-yl)urea, melting at 147°–148° C.

(78) trans-N-(2,6-diethylphenyl)-N'-cyclohexylmethyl-N'-(4-phenylcyclohexyl)urea, melting at 166°–167° C.

(79) trans-N-(2,6-diisopropylphenyl)-N'-cyclohexylmethyl-N'-(4-phenylcyclohexyl)urea, melting at 150°–152° C.

(80) cis-N-(2,6-diisopropylphenyl)-N'-(3-chlorobenzyl)-N'-(1,1'-bicyclohexyl-4-yl)urea, melting at 174°–176° C.

(81) cis-N-(2,6-diisopropylphenyl)-N'-(3-phenylpropyl)-N'-(1,1'-bicyclohexyl-4-yl)urea, melting at 148°–149.5° C.

(82) trans-N-(2,6-diisopropylphenyl)-N'-(4-trifluoromethylbenzyl)-N'-(4-phenylcyclohexyl)urea ½hydrate, melting at 172°–174° C.

(83) N-(2,6-diisopropylphenyl)-N'-(2-morpholinoethyl)-N'-(4-phenylcyclohexyl)urea ½hydrate, melting at 174°–176° C.

(84) N-(2,6-diisopropylphenyl)-N'-thenyl-N'-(4-phenylcyclohexyl)urea, melting at 150°–152° C.

(85) cis-N-(2,6-diisopropylphenyl)-N'-(3,4,5-trimethoxybenzyl)-N'-(1,1'-bicyclohexyl-4-yl)urea, amorphous

(86) cis-N-(2,6-diisopropylphenyl)-N'-(2-chloro-4-hydroxybenzyl)-N'-(1,1'-bicyclohexyl-4-yl)urea, melting at 168.5°–170° C.

(87) trans-N-(2,6-diisopropylphenyl)-N'-furfuryl-N'-(4-phenylcyclohexyl)urea, melting at 149°–151° C.

(88) cis-N-(2,6-diisopropylphenyl)-N'-(4-chlorobenzyl)-N'-(1,1'-bicyclohexyl-4-yl)urea, melting at 160°–161° C.

(89) cis-N-(2,6-diisopropylphenyl)-N'-(2-chlorobenzyl)-N'-(1,1'-bicyclohexyl-4-yl)urea, melting at 158°–160° C.

(90) N-(2,6-diethylphenyl)-N'-(2-methylbenzyl)-N'-(4-phenylcyclohexyl)urea, amorphous

(91) N-(2,6-diethylphenyl)-N'-(2-chlorobenzyl)-N'-(4-phenylcyclohexyl)urea, melting at 150°–151° C.

(92) trans-N-(2,6-diisopropylphenyl)-N'-(4-pyridylmethyl)-N'-(4-phenylcyclohexyl)urea ½hydrate, melting at 172°–173° C.

(93) trans-N-(2,6-diisopropylphenyl)-N'-(2-pyridylmethyl)-N'-(4-phenylcyclohexyl)urea hydrochloride ½hydrate, melting at 120°–122° C.

(94) trans-N-(2,6-diisopropylphenyl)-N'-(2,3-difluorobenzyl)-N'-(4-phenylcyclohexyl)urea, melting at 168°–170° C.

(95) trans-N-(2,6-diisopropylphenyl)-N'-(4-phenylbutyl)-N'-(4-phenylcyclohexyl)urea, melting at 151°–152° C.

(96) trans-N-(2,6-diisopropylphenyl)-N'-(2-ethoxybenzyl)-N'-(4-phenylcyclohexyl)urea, melting at 137°–138° C.

(97) trans-N-(2,6-diisopropylphenyl)-N'-(2-bromobenzyl)-N'-(4-phenylcyclohexyl)urea, melting at 188°–190° C.

(98) trans-N-(2,6-diisopropylphenyl)-N'-(2-fluorobenzyl)-N'-(4-phenylcyclohexyl)urea, melting at 157°–158° C.

(99) trans-N-(2,6-diisopropylphenyl)-N'-(2,3-dimethoxybenzyl)-N'-(4-phenylcyclohexyl)urea, melting at 160°–162° C.

(100) N-(2,6-diisopropylphenyl)-N'-(2-methoxyethyl)-N'-(4-phenylcyclohexyl)urea, melting at 141°–143° C.

(101) trans-N-(2,6-diisopropylphenyl)-N'-(2,6-difluorobenzyl)-N'-(4-phenylcyclohexyl)urea, melting at 166°–168° C.

(102) trans-N-(2,6-diisopropylphenyl)-N'-(2-hydroxybenzyl)-N'-(4-phenylcyclohexyl)urea, melting at 173°–175° C.

(103) trans-N-(2,6-diisopropylphenyl)-N'-(2-(2-chlorophenyl)ethyl)-N'-(4-phenylcyclohexyl)urea, melting at 145°–147° C.

(104) trans-N-(2,6-diisopropylphenyl)-N'-(3-(2-chlorophenyl)propyl)-N'-(4-phenylcyclohexyl)urea, melting at 200°–202° C.

(105) trans-N-(2,6-diisopropylphenyl)-N'-(2-methylthiobenzyl)-N'-(4-phenylcyclohexyl)urea, melting at 159.5°–181° C.

(106) trans-N-(2,6-diisopropylphenyl)-N'-(2-benzyloxybenzyl)-N'-(4-phenylcyclohexyl)urea, melting at 158.5°–160° C.

(107) trans-N-(2,6-diisopropylphenyl)-N'-(2-(2-methylphenyl)ethyl)-N'-(4-phenylcyclohexyl)urea, melting at 122°–123° C.

(108) trans-N-(2,6-diisopropylphenyl)-N'-(2-benzylthiobenzyl)-N'-(4-phenylcyclohexyl)urea, melting at 177°–178° C.

(109) trans-N-(2,4,6-tri-tert-butylphenyl)-N'-benzyl-N'-(4-phenylcyclohexyl)urea (110) trans-N-(2,6-diisopropylphenyl)-N'-(3-(2-methylphenyl)propyl)-N'-(4-phenylcyclohexyl)urea, melting at 118° C.

(111) trans-N-(2,6-diisopropylphenyl)-N'-(4-(2-chlorophenyl)butyl)-N'-(4-phenylcyclohexyl)urea (112) trans-N-(2,6-diethylphenyl)-N'-(2-(2-methylphenyl)ethyl)-N'-(4-phenylcyclohexyl)urea (113) trans-N-(2,6-diisopropylphenyl)-N'-(4-hydroxy-3,5-di-tert-butyl-benzyl)-N'-(4-phenylcyclohexyl)urea (114) trans-N-(2,6-diisopropylphenyl)-N'-(2-(2-chlorophenoxy)ethyl)-N'-(4-phenylcyclohexyl)urea (115) trans-N-(2,6-dimethylphenyl)-N'-benzyl-N'-(4-phenylcyclohexyl)urea, melting at 119°–121° C.

(116) trans-N-(2,6-diisopropylphenyl)-N'-(4-(2-methylphenyl)butyl)-N'-(4-phenylcyclohexyl)urea (117) trans-N-(2,6-diethylphenyl)-N'-(2-(2-chlorophenyl)ethyl)-N'-(4-phenylcyclohexyl)urea (118) trans-N-(2,4,6-trimethoxyphenyl)-N'-(2-(2-methylphenyl)ethyl)-N'-(4-phenylcyclohexyl)urea (119) trans-N-(2,6-diisopropylphenyl)-N'-(2-ethylbenzyl)-N'-(4-phenylcyclohexyl)urea (120) cis-N-(2,6-diisopropylphenyl)-N'-(2-methoxybenzyl)-N'-(4-phenylcyclohexyl)urea, melting at 145°–146.5° C.

(121) trans-N-(2,6-diisopropylphenyl)-N'-(3-chlorobenzyl)-N'-(4-phenylcyclohexyl)urea, melting at 174°–175.5° C.

(122) trans-N-(2,6-diisopropylphenyl)-N'-(4-chlorobenzyl)-N'-(4-phenylcyclohexyl)urea, melting at 197°–198.5° C.

(123) trans-N-(2,6-diisopropylphenyl)-N'-(2-methoxybenzyl)-N'-(4-phenylcyclohexyl)urea, melting at 154°–155° C.

(124) trans-N-(2,6-diisopropylphenyl)-N'-(3-(3,4-dimethoxyphenyl)-propyl)-N'-(4-phenylcyclohexyl)urea, melting at 176.5°–178° C.

(125) trans-N-(2,6-diisopropylphenyl)-N'-(2,3,4-trimethoxybenzyl)-N'-(4-phenylcyclohexyl)urea, melting at 127°–128° C.

(126) trans-N-(2,6-diisopropylphenyl)-N'-(4-propoxybenzyl)-N'-(4-phenylcyclohexyl)urea, melting at 145°–147° C.

(127) trans-N-(2,6-diisopropylphenyl)-N'-(2-(3,4-dimethoxyphenyl)-ethyl)-N'-(4-phenylcyclohexyl)urea, melting at 144°–145° C.

(128) trans-N-(2,6-diisopropylphenyl)-N'-(3-methyl-2-thenyl)-N'-(4-phenylcyclohexyl)urea, melting at 143° C.

(129) trans-N-(2,6-diisopropylphenyl)-N'-(4-t-buthylbenzyl)-N'-(4-phenylcyclohexyl)urea, melting at 175°–176° C.

(130) trans-N-(2,6-diisopropylphenyl)-N'-(2,4,6-trimethoxybenzyl)-N'-(4-phenylcyclohexyl)urea, melting at 142°–143° C.

(131) trans-N-(2,6-diisopropylphenyl)-N'-(4-isopropylbenzyl)-N'-(4-phenylcyclohexyl)urea, melting at 176°–178° C.

(132) trans-N-(2,6-diisopropylphenyl)-N'-(4-hexyloxybenzyl)-N'-(4-phenylcyclohexyl)urea, melting at 123°–124° C.

(133) trans-N-(2,6-diisopropylphenyl)-N'-(6-methyl-2-pyridylmethyl)-N'-(4-phenylcyclohexyl)urea hydrochloride 5/4hydrate, amorphous powder (134) trans-N-(2,6-diisopropylphenyl)-N'-(2-(2-pyridyl)ethyl)-N'-(4-phenylcyclohexyl)urea hydrochloride hydrate, melting at 169°–171° C.

(135) trans-N-(2,6-diisopropylphenyl)-N'-(thiazol-2-ylmethyl)-N'-(4-phenylcyclohexyl)urea, melting at 128°–129° C.

(136) trans-N-(2,6-diisopropylphenyl)-N'-(5-methyl-2-furylmethyl)-N'-(4-phenylcyclohexyl)urea, melting at 160°–161° C.

(137) trans-N-(2,6-diisopropylphenyl)-N'-(2-imidazolylmethyl)-N'-(4-phenylcyclohexyl)urea hydrochloride hydrate, melting at 178°–180° C.

(138) trans-N-(3-trifluoromethylphenyl)-N'-benzyl-N'-( 4-phenylcyclohexyl)urea, melting at 184°–185° C.

(139) trans-N-(2,6-dimethylphenyl)-N'-(2-fluorobenzyl)-N'-(4-phenylcyclohexyl)urea, melting at 100°–102° C.

(140) trans-N-(2,6-diisopropylphenyl)-N'-(3-pyridylmethyl)-N'-(4-phenylcyclohexyl)urea hydrochloride hydrate, amorphous powder (141) trans-N-(2,6-diisopropylphenyl)-N'-(3-pyridylmethyl)-N'-(4-phenylcyclohexyl)urea, melting at 175°–176.5° C.

(142) trans-N-(2,4-dimethoxyphenyl)-N'-benzyl-N'-(4-phenylcyclohexyl)urea, melting at 161°–162° C.

(143) cis-N-(2,4-difluorophenyl)-N'-benzyl-N'-(1,1'-bicyclohexyl-4-yl)urea, melting at 122°–123° C.

(144) trans-N-(2,6-diisopropylphenyl)-N'-(1-benzylpiperidin-4 -yl)methyl-N'-(4-phenylcyclohexyl)urea, $^1$H-NMR (CDCl$_3$) δ (ppm): 1.20(12H,t,J=7 Hz), 1.40–3.33(22H,m), 3.73–4.01(1H,m), 4.09(2H,brs), 5.65(1H,m), 6.95–7.63(13H,m)

(145) cis-N-(2,6-dimethylphenyl)-N'-benzyl-N'-(1,1'-bicyclohexyl-4yl)urea, melting at 148°–150° C.

(146) trans-N-(2,6-dimethylphenyl)-N'-(3-fluoropyridin-2-yl)methyl-N'-(4-phenylcyclohexyl)urea hydrochloride ½hydrate, melting at 202°–204° C.

(147) cis-N-(2,6-dimethylphenyl)-N'-(2-pyridylmethyl)-N'-(1,1'-bicyclohexyl-4-yl)urea (148) cis-N-(2,6-dimethylphenyl)-N'-(3-hydroxypyridin-2-yl)methyl-N'-(1,1'-bicyclohexyl-4-yl)urea (149) trans-N-(2,6-dimethylphenyl)-N'-(2-ethoxyethyl)-N'-(1,1'-bicyclohexyl-4-yl)urea (150) cis-N-(2,6-dimethylphenyl)-N'-[2-(4-hydroxy-2,3,5-trimethylphenoxy)ethyl]-N'-(1,1'-bicyclohexyl-4-yl)urea (151) cis-N-(2,6-dimethylphenyl)-N'-(2-butylthioethyl)-N'-(1,1'-bicyclohexyl-4-yl)urea (152) trans-N-(2,6-dimethylphenyl)-N'-(2-phenoxyethyl)-N'-(1,1'-bicyclohexyl-4yl)urea (153) cis-N-(2,6-dimethylphenyl)-N'-heptyl-N'-(1,1'-bicyclohexyl-4-yl)urea (154) cis-N-(2,6-dimethylphenyl)-N'-(2,4-dimethoxybenzyl)-N'-(1,1'-bicyclohexyl-4-yl)urea (155) cis-N-(2,6-dimethylphenyl)-N'-(2-hydroxybenzyl)-N'-(1,1'-bicyclohexyl-4-yl)urea (156) cis-N-(2,5-dimethoxyphenyl)-N'-(2-hydroxybenzyl)-N'-(1,1'-bicyclohexyl-4-yl)urea (157) cis-N-(2,5-dimethoxyphenyl)-N'-benzyl-N'-(1,1'-bicyclohexyl-4-yl)urea (158) trans-N-(2,5-dimethylphenyl)-N'-benzyl-N'-(1,1'-bicyclohexyl-4-yl)urea (159) cis-N-(2,4,6-trimethylphenyl)-N'-benzyl-N'-(1,1'-bicyclohexyl-4-yl)urea (160) cis-N-(2,5-difluorophenyl)-N'-benzyl-N'-(1,1'-bicyclohexyl-4-yl)urea (161) cis-N-(2,4-dimethoxyphenyl)-N'-benzyl-N'-(1,1'-bicyclohexyl-4-yl)urea (162) cis-N-(2,4,6-trimethoxyphenyl)-N'-(2,4-dimethoxybenzyl)-N'-(1,1'-bicyclohexyl-4-yl)urea (163) trans-N-(2,6-diethylphenyl)-N'-(2-butylthioethyl)-N'-(1,1'-bicyclohexyl-4-yl)urea (164) cis-N-(2,6-diethylphenyl)-N'-(2,4-dimethoxybenzyl)-N'-(1,1'-bicyclohexyl-4-yl)urea (165) trans-N-(2,6-difluorophenyl)-N'-benzyl-N'-(1,1'-bicyclohexyl-4-yl)urea (166) cis-N-(2,6-dichlorophenyl)-N'-benzyl-N'-(1,1'-bicyclohexyl-4-yl)urea (167) cis-N-(2,5-dichlorophenyl)-N'-benzyl-N'-(1,1'-bicyclohexyl-4-yl)urea (168) cis-N-(2,4-chlorophenyl)-N'-benzyl-N'-(1,1'-bicyclohexyl-4-yl)urea (169) cis-N-(2,6-dimethylphenyl)-N'-(2-thenyl)-N'-(1,1'-bicyclohexyl-4-yl)urea (170) cis-N-(2,6-dimethylphenyl)-N'-(2-fluorobenzyl)-N'-(1,1'-bicyclohexyl-4-yl)urea (171) trans-N-(2,6-diisopropylphenyl)-N'-(2-butylthioethyl)-N'-(1,1'-bicyclohexyl-4-yl)urea (172) cis-N-(2,4-difluorophenyl)-N'-heptyl-N'-(1,1'-bicyclohexyl-4-yl)urea (173) trans-N-(2,6-dichlorophenyl)-N'-benzyl-N'-(4-phenylcyclohexyl)urea (174) trans-N-(2,5-dichlorophenyl)-N'-benzyl-N'-(4-phenylcyclohexyl)urea (175) trans-N-(2,4-dichlorophenyl)-N'-benzyl-N'-(4-phenylcyclohexyl)urea (176) trans-N-(2,6-dimethylphenyl)-N'-(2-pyrrolyl)-methyl-N'-(4-phenylcyclohexyl)urea (177) trans-N-(2,6-dimethylphenyl)-N'-pyrazinylmethyl-N'-(4-phenylcyclohexyl)urea (178) trans-N-(2,6-dimethylphenyl)-N'-(2-pyrimidinyl)methyl-N'-(4-phenylcyclohexyl)urea (179) trans-N-(4-dimethylaminophenyl)-N'-benzyl-N'-(4-phenylcyclohexyl)urea (180) trans-N-(2,6-dichlorophenyl)-N'-benzyl-N'-(4-t-butylcyclohexyl)urea (181) trans-N-(2,5-dichlorophenyl)-N'-benzyl-N'-(4-t-butylcyclohexyl)urea (182) trans-N-(2,4-dichlorophenyl)-N'-benzyl-N'-(4-t-butylcyclohexyl)urea (183) trans-N-(2,6-dimethoxyphenyl)-N'-benzyl-N'-(4-t-butylcyclohexyl)urea (184) cis-N-(4-hydroxy-2,3,5-trimethylphenyl)-N'-benzyl-N'-(1,1'-bicyclohexyl-4-yl)urea (185) cis-N-(2-hydroxy-5-methylphenyl)-N'-benzyl-N'-(1,1'-bicyclohexyl-4-yl)urea (186) cis-N-(3,5-dimethyl-4-pyridyl)-N'-benzyl-N'-(1,1'-bicyclohexyl-4-yl)urea (187) cis-N-(4,6-dimethyl-2-pyridyl)-N'-benzyl-N'-(1,1'-bicyclohexyl-4-yl)urea (188) cis-N-(2,4-dimethyl-3-pyridyl)-N'-benzyl-N'-(1,1'-bicyclohexyl-4-yl)urea (189) cis-N-(2,4-dimethylthio-3-pyridyl)-N'-benzyl-N'-(1,1'-bicyclohexyl-4-yl)urea (190) cis-N-(4-methyl-2-thiazolyl)-N'-benzyl-N'-(1,1'-bicyclohexyl-4-yl)urea (191) cis-N-(2-methylthio-5-butylcarbamoylphenyl)-N'-benzyl-N'-(1,1'-bicyclohexyl-4-yl)urea Example of Pharmaceutical Composition The tablets containing the compound of formula (I) can be prepared by the following formulation.

| | |
|---|---|
| Compound (I) | 100 mg |
| Lactose | 76 mg |

-continued

| | |
|---|---|
| Corn starch | 10 mg |
| Carboxymethylcellulose calcium | 5 mg |
| Methylcellulose | 3 mg |
| Magnesium stearate | 2 mg |
| Polyvinyl pyrrolidone | 4 mg |
| Total | 200 mg |

Compound (I) is crushed with an atomizer to make fine powder having an average particle size below 10μ. The fine powder of Compound (I), lactose, corn starch, carboxymethylcellulose calcium and methylcellulose are mixed well in a kneader and then kneaded with a binder prepared by polyvinyl pyrrolidone. The wet mass is passed through a 200 mesh sieve to give granules and then dried in an oven at 50° C. The dry granules containing 3–4% of water content is forced through a 24 mesh sieve. Magnesium stearate is mixed with and compressed into tablets by using a rotatory tableting machine with a flat punch of 8 mm diameter.

We claim:

1. A cyclohexylurea compound of the formula (I):

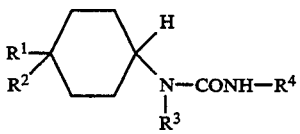

wherein;
R$^1$ is phenyl; R$^2$ is hydrogen; R$^3$ is alkyl having 1 to 8 carbon atoms, cyclohexylmethyl, aralkyl, aralkyl substituted on the aromatic ring by 1 to 3 substituents selected from alkyl having 1 to 4 carbon atoms, alkoxy having 1 to 5 carbon atoms and halogen; R$^4$ is phenyl substituted by 1 to 3 substituents selected from alkyl having 1 to 4 carbon atoms, alkoxy having 1 to 4 carbon atoms and halogen; or a pharmaceutically acceptable salt thereof.

2. The compound as claimed in claim 1 selected from the group consisting of

N-(2,6-diisopropylphenyl)-N'-heptyl-N'-(4-phenylcyclohexyl)urea,
N-(2,6-diisopropylphenyl)-N'-benzyl-N'-(4-phenylcyclohexyl)urea,
N-(2,6-diethylphenyl)-N'-cyclohexylmethyl-N'-(4-phenylcyclohexyl)urea,
cis-N-(2,6-diisopropylphenyl)-N'-benzyl-N'-(4-phenylcyclohexyl)urea,
trans-N-(2,6-diisopropylphenyl)-N'-benzyl-N'-(4-phenylcyclohexyl)urea,
N-(2,6-diethylphenyl)-N'-benzyl-N'-(4-phenylcyclohexyl)urea,
N-(2,4-difluorophenyl)-N'-benzyl-N'-(4-phenylcyclohexyl)urea,
N-(2,4,6-trimethoxyphenyl)-N'-benzyl-N'-(4-phenylcyclohexyl)urea,
trans-N-(2,6-diisopropylphenyl)-N'-(2-methylbenzyl)-N'-(4-phenylcyclohexyl)urea,
trans-N-(2,6-diisopropylphenyl)-N'-(2-chlorobenzyl)-N'-(4-phenylcyclohexyl)urea,
N-(2,6-diisopropylphenyl)-N'-(3-phenylpropyl)-N'-(4-phenylcyclohexyl)urea,
N-(2,6-diisopropylphenyl)-N'-(2-phenylethyl)-N'-(4-phenylcyclohexyl)urea,
trans-N-(2,6-diisopropylphenyl)-N'-(3-phenylpropyl)-N'-(4-phenylcyclohexyl)urea,
trans-N-(2,6-diethylphenyl)-N'-cyclohexylmethyl-N'-(4-phenylcyclohexyl)urea,
trans-N-(2,6-diisopropylphenyl)-N'-cyclohexylmethyl-N'-(4-phenylcyclohexyl)urea,
N-(2,6-diethylphenyl)-N'-(2-methylbenzyl)-N'-(4-phenylcyclohexyl)urea,
N-(2,6-diethylphenyl)-N'-(2-chlorobenzyl)-N'-(4-phenylcyclohexyl)urea,
trans-N-(2,6-diisopropylphenyl)-N'-(4-phenylbutyl)-N'-(4-phenylcyclohexyl)urea,
trans-N-(2,6-diisopropylphenyl)-N'-(4-ethoxybenzyl)-N'-(4-phenylcyclohexyl)urea,
trans-N-(2,6-diisopropylphenyl)-N'-(2-fluorobenzyl)-N'-(4-phenylcyclohexyl)urea,
trans-N-(2,6-diisopropylphenyl)-N'-(2,6-difluorobenzyl)-N'-(4-phenylcyclohexyl)urea,
trans-N-(2,6-diisopropylphenyl)-N'-(2-(2-chlorophenyl)ethyl)-N'-(4-phenylcyclohexyl)urea,
trans-N-(2,6-diisopropylphenyl)-N'-(2-(2-methylphenyl)ethyl)-N'-(4-phenylcyclohexyl)urea,
trans-N-(2,6-dimethylphenyl)-N'-benzyl-N'-(4-phenylcyclohexyl)urea,
trans-N-(2,6-diisopropylphenyl)-N'-(3-chlorobenzyl)-N'-(4-phenylcyclohexyl)urea,
trans-N-(2,6-diisopropylphenyl)-N'-(2-methoxybenzyl)-N'-(4-phenylcyclohexyl)urea, and
trans-N-(2,6-diisopropylphenyl)-N'-(4-t-butylbenzyl)-N'-(4-phenylcyclohexyl)urea,
or a pharmaceutically acceptable salt thereof.

3. The compound as claimed in claim 1 having the formula:

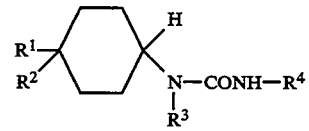

wherein;
R$^1$ is phenyl; R$^2$ is hydrogen; R$^3$ is heptyl, cyclohexylmethyl, benzyl or benzyl substituted on the aromatic ring by 1 to 3 substituents selected from alkyl having 1 to 4 carbon atoms, methoxy and halogen; R$^4$ is phenyl substituted by 1 to 3 substituents selected from alkyl having 1 to 4 carbon atoms, methoxy and halogen; or a pharmaceutically acceptable salt thereof.

4. The compound as claimed in claim 1 selected from the group consisting of:

N-(2,6-diisopropylphenyl)-N'-heptyl-N'-(4-phenylcyclohexyl)urea,
N-(2,6-diethylphenyl)-N'-cyclohexylmethyl-N'-(4-phenylcyclohexyl)urea,
trans-N-(2,6-diisopropylphenyl)-N'-benzyl-N'-(4-phenylcyclohexyl)urea,
N-(2,6-diethylphenyl)-N'-benzyl-N'-(4-phenylcyclohexyl)urea,
N-(2,4,6-trimethoxyphenyl)-N'-benzyl-N'-(4-phenylcyclohexyl)urea,
trans-N-(2,6-diisopropylphenyl)-N'-(2-methylbenzyl)-N'-(4-phenylcyclohexyl)urea,
trans-N-(2,6-diisopropylphenyl)-N'-(2-chlorobenzyl)-N'-(4-phenylcyclohexyl)urea,
trans-N-(2,6-diethylphenyl)-N'-cyclohexylmethyl-N'-(4-phenylcyclohexyl)urea,
trans-N-(2,6-diisopropylphenyl)-N'-(2-fluorobenzyl)-N'-(4-phenylcyclohexyl)urea, and trans-N-(2,6-dimethylphenyl)-N'-benzyl-N'-(4-phenylcyclohexyl)urea, or a pharmaceutically acceptable salt thereof.

5. The compound as claimed in claim 1 having the formula:

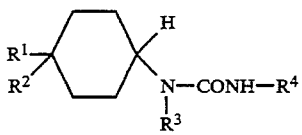

wherein;

R$^1$ is phenyl; R$^2$ is hydrogen; R$^3$ is cyclohexylmethyl, benzyl or benzyl substituted on the aromatic ring by 1 to 3 substituents selected from methyl, methoxy and halogen; R$^4$ is phenyl substituted by 1 to 3 substituents selected from alkyl having 1 to 4 carbon atoms and methoxy; or a pharmaceutically acceptable salt thereof.

6. The compound as claimed in claim 1 selected from the group consisting of:

N-(2,6-diethylphenyl)-N'-cyclohexylmethyl-N'-(4-phenylcyclohexyl)urea, trans-N-(2,6-diisopropylphenyl)-N'-benzyl-N'-(4-phenylcyclohexyl)urea, N-(2,6-diethylphenyl)-N'-benzyl-N'-(4-phenylcyclohexyl)urea, trans-N-(2,6-diisopropylphenyl)-N'-(2-methylbenzyl)-N'-(4-phenylcyclohexyl)urea, trans-N-(2,6-diisopropylphenyl)-N'-(2-chlorobenzyl)-N'-(4-phenylcyclohexyl)urea, trans-N-(2,6-diethylphenyl)-N'-cyclohexylmethyl-N'-(4-phenylcyclohexyl)urea, trans-N-(2,6-diisopropylphenyl)-N'-(2-fluorobenzyl)-N'-(4-phenylcyclohexyl)urea, and trans-N-(2,6-dimethylphenyl)-N'-benzyl-N'-(4-phenylcyclohexyl)urea, or a pharmaceutically acceptable salt thereof.

7. A pharmaceutical composition consisting of an effective amount of the compound as claimed in claim 1 or a pharmaceutically acceptable salt thereof and a pharmaceutical carries.

8. Trans-N-(2,6-dimethylphenyl)-N'-benzyl-N'-(4-phenyl-cyclohexyl)urea, or a pharmaceutically acceptable salt thereof.

* * * * *